(12) United States Patent
Feger et al.

(10) Patent No.: US 7,516,674 B1
(45) Date of Patent: Apr. 14, 2009

(54) METHOD AND APPARATUS FOR THERMALLY INDUCED TESTING OF MATERIALS UNDER TRANSIENT TEMPERATURE

(75) Inventors: Claudius Feger, Poughkeepsie, NY (US); Soojae Park, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 12/198,479

(22) Filed: Aug. 26, 2008

(51) Int. Cl.
*G01N 19/08* (2006.01)
(52) U.S. Cl. .......................................... 73/799; 73/808
(58) Field of Classification Search .................... 73/799, 73/808–815
See application file for complete search history.

(56) References Cited

U.S. PATENT DOCUMENTS

| | | | |
|---|---|---|---|
| 5,980,103 A * | 11/1999 | Ikuno et al. | 374/57 |
| 6,520,024 B2 | 2/2003 | Nihei et al. | |
| 6,935,187 B1 * | 8/2005 | Gorman et al. | 73/811 |
| 7,331,242 B2 * | 2/2008 | Kim | 73/766 |
| 2005/0146708 A1 | 7/2005 | Shi et al. | |
| 2005/0178209 A1 * | 8/2005 | Kim | 73/803 |

FOREIGN PATENT DOCUMENTS

JP        8178816      7/1996

OTHER PUBLICATIONS

Abstract of JP8178816.

* cited by examiner

*Primary Examiner*—Max Noori
(74) *Attorney, Agent, or Firm*—Cahn & Samuels, LLP

(57) ABSTRACT

A method for measuring the fracture and fatigue crack growth behavior of a material includes heating at least one sample having a first end and a second end and a pre-applied crack between the first end and the second end; heating a fixture having a lower coefficient of thermal expansion than said at least one sample; attaching the first end and the second end of the at least one sample to the fixture; cooling the at least one sample and fixture; recording the temperature at which propagation of the pre-applied crack through the width of the at least one sample occurs as the critical fracture temperature; for a plurality of samples, each sample having a different ratio of pre-applied crack length to sample width, determining the critical fracture temperature as a function of said ratio; and ranking materials by the critical fracture temperature.

1 Claim, 5 Drawing Sheets

METHOD AND APPARATUS FOR THERMALLY INDUCED TESTING OF MATERIALS UNDER TRANSIENT TEMPERATURE

FIELD OF THE INVENTION

This invention relates to a method and apparatus that measures the fracture behavior of materials by application of thermally induced stresses.

BACKGROUND OF THE INVENTION

The selection of materials for engineering applications requires characterization of the fracture behavior of these materials, since the reliability of the resulting product or structure depends on the materials' ability to resist applied loads and stresses. The properties most important for such applications are fracture toughness and fatigue resistance.

Numerous laboratory tests have been developed to determine the fracture toughness of a material by applying mechanical stress. The results of such tests have been used to rank materials for material selection by fracture toughness. However, these tests are performed at an isothermal temperature.

It is generally assumed that the fracture behavior measured by these tests describes the fracture behavior in situations where the stress is applied by heating or cooling. Temperature induced stresses are very common in areas such as aerospace, automotive, civil, electronic and consumer applications and occur in all parts or structures in which at least two materials with differing coefficients of thermal expansion (CTE) are present. During heating or cooling, the materials expand at differing rates thus experiencing gradual or incremental changes in loading and stress. There is experimental evidence that the fracture toughness measured by mechanically induced, isothermal testing inadequately describes the fracture behavior of parts that experience temperature changes.

In cases in which many materials are being screened for an application, it is time consuming to identify the exact fracture toughness of each material. Moreover, other properties such as the relaxation modulus and the CTE of the considered materials must be evaluated as well.

There remains a need for a method to measure the fracture toughness and fatigue resistance for materials for transient temperature environments and to rank such materials.

SUMMARY OF THE INVENTION

According to an aspect of the present invention, a method for measuring the fracture and fatigue crack growth behavior of a material is provided. At least one sample having a first end and a second end and a pre-applied crack between the first end and the second end is heated. A fixture having a lower coefficient of thermal expansion than the at least one sample is heated. The first end and the second end of the at least one sample is attached to the fixture. The at least one sample and fixture are cooled. The temperature at which propagation of the pre-applied crack through the width of the at least one sample occurs is recorded as the critical fracture temperature. For a plurality of samples, each sample having a different ratio of pre-applied crack length to sample width, the critical fracture temperature as a function of the ratio is determined, and the materials are ranked by the critical fracture temperature.

According to another aspect of the invention, an apparatus for conducting a thermally induced fracture test is provided comprising an environmental chamber into which at least one sample and fixture are placed, wherein the at least one sample has a first end and a second end and a pre-applied crack between the first end and the second end. The apparatus also includes a dispenser for dispensing an adhesive onto the ends of the at least one sample, the ends of the fixture, or both; an automated data acquisition and computing device for recording the temperature of the environmental chamber and the length of the crack; and an electrically conductive line placed on the at least one sample and comprising an electrically conductive composite or a metal.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

Given the following enabling description of the drawings, the apparatus and methods should become evident to a person of ordinary skill in the art.

BRIEF DESCRIPTION OF THE DRAWINGS

FIG. 1 is a schematic diagram of a specimen for a thermally induced fracture test having width W, length L, and crack length, a.

DETAILED DESCRIPTION OF THE INVENTION

FIGS. 1-5 illustrate a method and apparatus for measuring the fracture behavior of materials by application of thermally induced stresses. According to the present invention, using a critical fracture temperature to measure thermally induced fracture toughness, materials may be ranked based on a combination of properties that include modulus, CTE, and fracture toughness. Since stresses tend to increase most strongly during cooling, the following discussion is directed to a method using cooling; however, changes that occur during heating may be utilized according to the invention.

According to the present invention, the critical fracture temperature of a material ($T_c$) is measured as follows.

At least one sample having a pre-applied crack is affixed at an elevated temperature to a fixture or frame that has a lower coefficient of thermal expansion and a higher modulus than the at least one sample. In embodiments, the at least one sample may comprise a material such as a polymer. In embodiments, the fixture may comprise a material such as a metal (e.g., stainless steel, nickel), a metal alloy (e.g., Invar), a ceramic, or any combination thereof.

Figure 1:
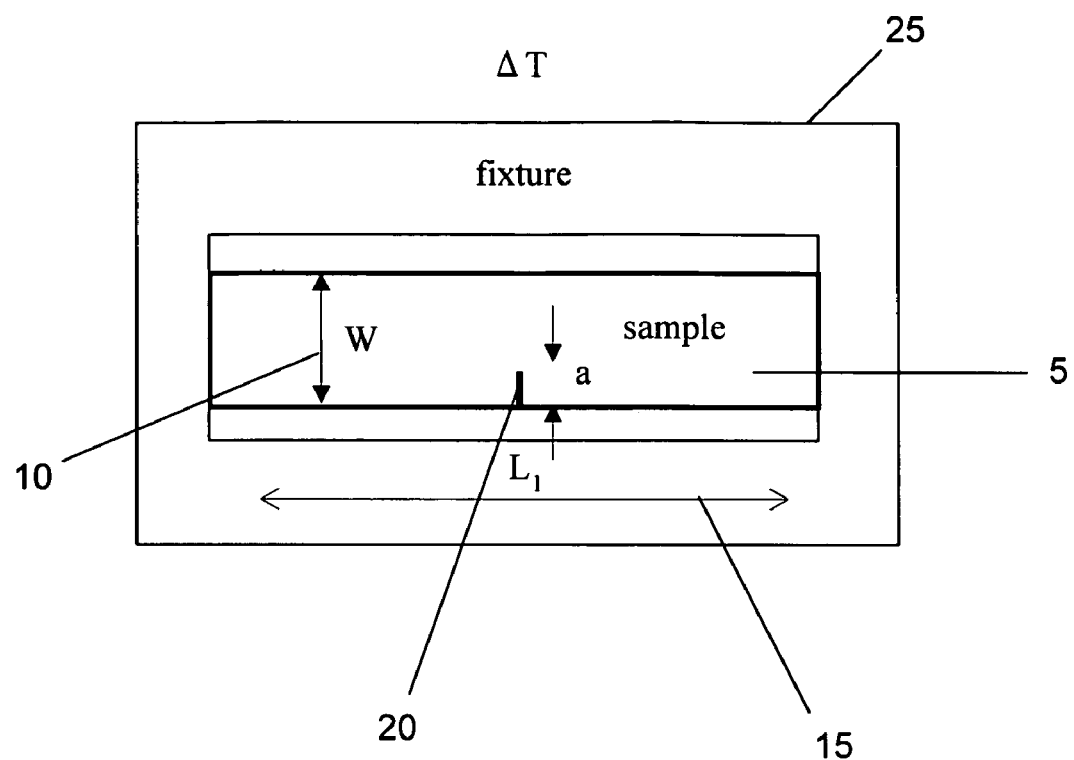

As illustrated in FIG. 1, the at least one sample 5 has a width W (10), and length L (15), and a pre-applied crack a (20) and is affixed to fixture 25. Both ends of the sample 5 are fastened or bonded to the fixture 25 to constrain free contraction during cooling or heating.

Figures 2A, 2B:
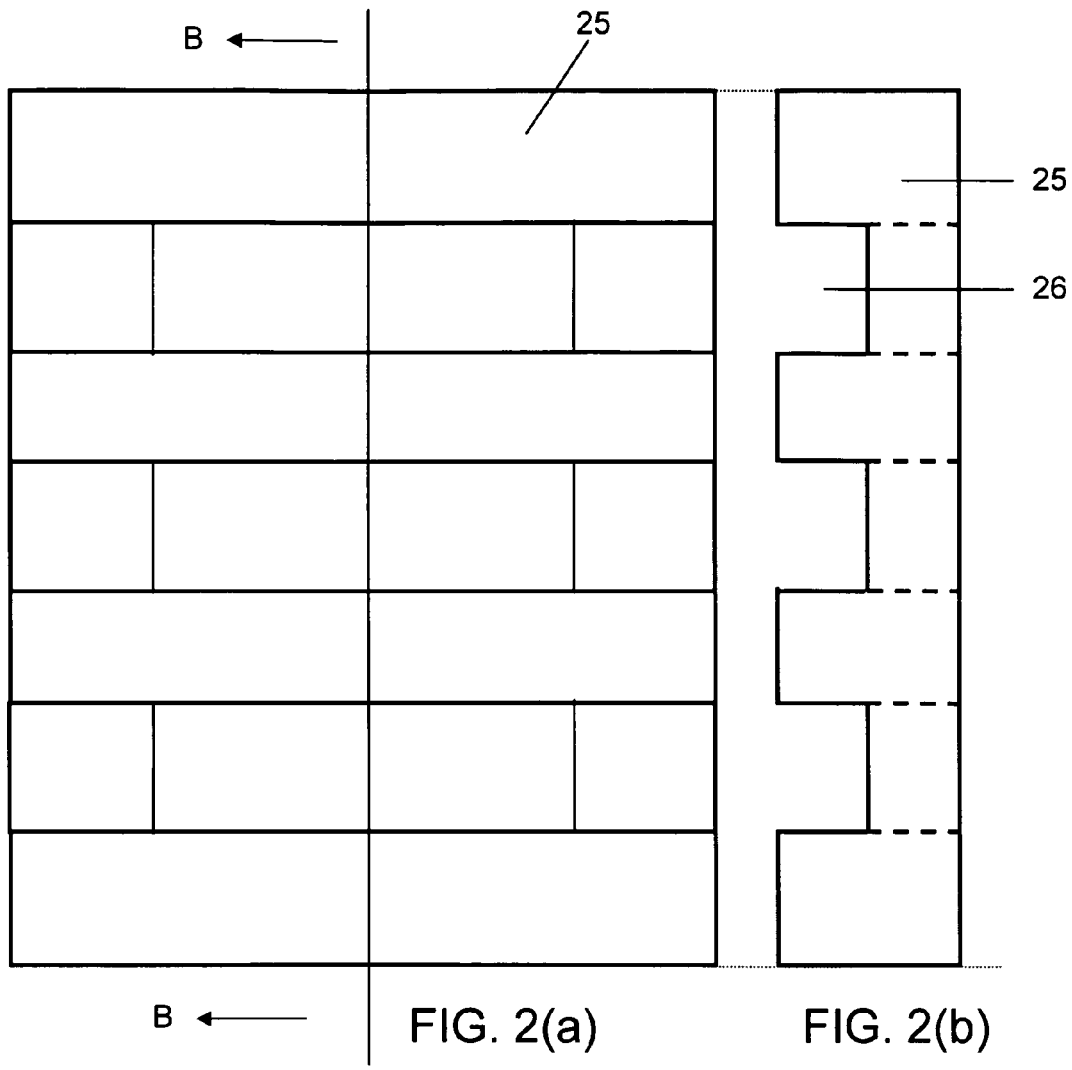
FIGS. 2(a) and 2(b) are schematic diagrams showing a fixture according to an embodiment of the present invention.

The fixture may hold at least one sample, for example, two or more samples. FIG. 2a is a schematic diagram showing a fixture 25 according to an embodiment of the present invention which allows for measurement of the critical fracture temperature for a plurality of sample (i.e., 3 samples). FIG. 2b is a cross section view of the fixture showing grooves 26 for the samples. The samples typically have a common width, length, and thickness and have a pre-applied crack of various lengths applied to the center or another suitable location of each sample.

Figure 4:
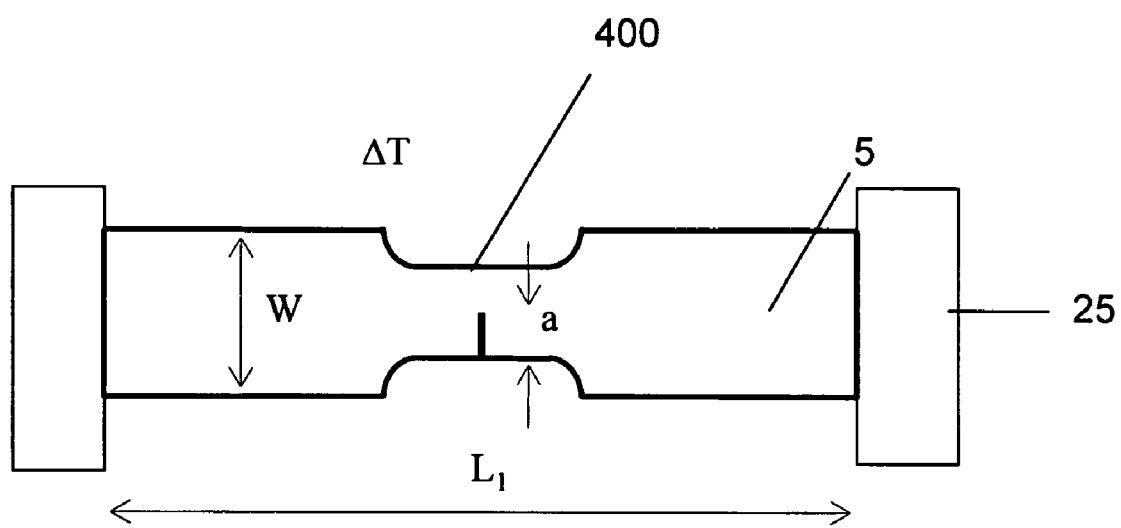
FIG. 4 is a schematic diagram of a sample having a dog-bone shape according to an embodiment of the present invention.
Figure 5:
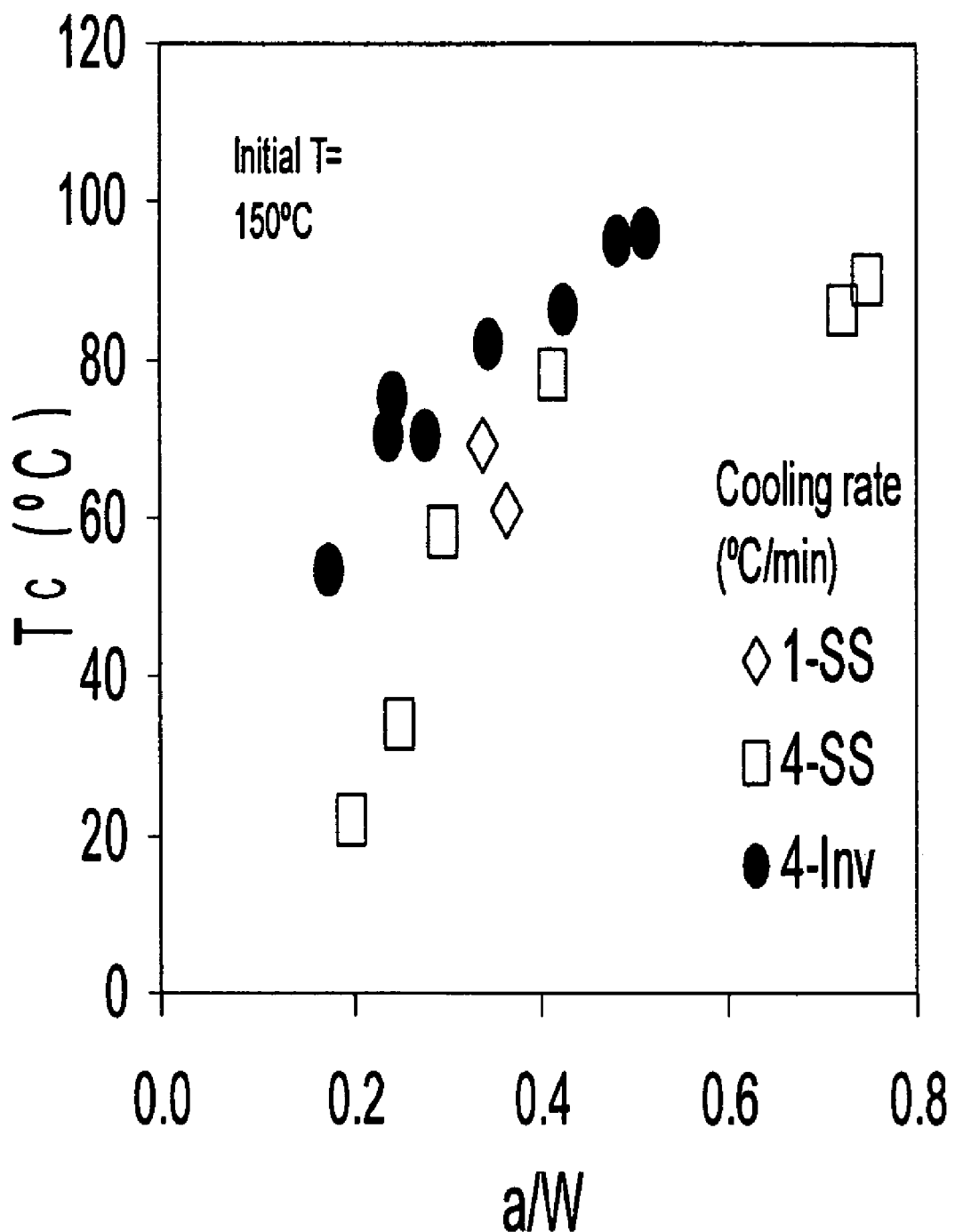
FIG. 5 is a graph of critical fracture temperature versus a/W according to an embodiment of the present invention.

The shape of the at least one sample may be rectangular as illustrated in FIG. 1, but may be of a different shape as long as it is attached to a fixture in a manner to constrain free contraction during heating or cooling. FIG. 4 illustrates a sample having a dog-bone shape which is optimized to adjust to the level of toughness expected for the sample material.

After the at least one sample having a pre-applied crack is affixed at an elevated temperature to the fixture, the temperature is lowered for the at least one sample and fixture substantially simultaneously. The length of the pre-applied crack is monitored during temperature change. The length of the crack can be monitored by any method known to those skilled in the art. In embodiments, the monitoring can be done visually by the unaided or aided eye, or by a video camera with or without optical pattern recognition software. In other embodiments, an electrically conductive line may be applied to a surface of the at least one sample perpendicular to the crack direction so that the electrically conducting path will be broken when the at least one sample fractures.

The cooling produces a tensile stress on the at least one sample. The thermal tensile stress in the at least one sample increases with increasing CTE mismatch between the at least one sample and the fixture, sample stiffness, and temperature change. When the thermal stress increases to reach the at least one sample's resistance to crack growth (fracture toughness), the pre-applied crack starts to grow and the at least one sample ruptures. According to the present invention, the critical fracture temperature is defined as the temperature at which crack growth is triggered.

Figure 3:
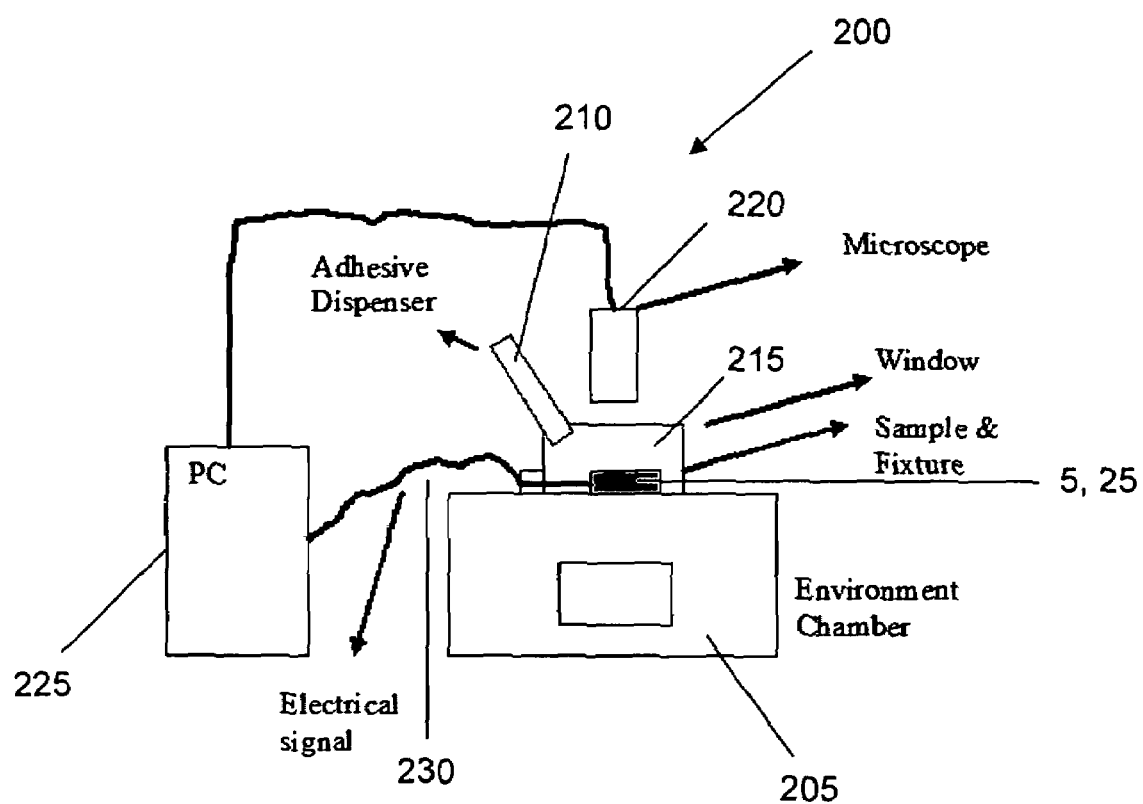
FIG. 3 is a schematic diagram of an apparatus for conducting a thermally induced fracture test according to an embodiment of the present invention.

FIG. 3 is a schematic diagram of an apparatus 200 for conducting a thermally induced fracture test according to an embodiment of the present invention. The apparatus 200 comprises an environmental chamber 205 into which at least one sample 5 and fixture 25 are placed. The environmental chamber is capable of keeping an isothermal temperature, and also allows for heating and cooling of the at least one sample and fixture at various rates.

To aid in fastening both ends of the at least one sample 5 to the fixture 25, the apparatus 200 may be equipped with a dispenser 210 capable of dispensing an adhesive onto the ends of the at least one sample, the ends of the fixture, or both. Dispenser 210 may be a permanent fixture of the apparatus. Alternatively, the dispenser may be a separate device allowing for manual application of adhesive. In embodiments, instead of using adhesive, the at least one sample may be attached or bonded to the fixture using clamps. Alternatively, a hole in each end of the at least one sample may be aligned with pins in the fixture. If pins are used, one pin may be fixed and the other pin may be adjustable. As the at least one sample expands during the initial heating, the adjustable pin would slide, but would be fastened to its maximum position once the starting temperature is reached.

In embodiments, the apparatus 200 may be equipped with a pick and place automaton that places the sample onto the fixture. A light source inside or outside the environmental chamber 205 may be used to illuminate the at least one sample. The environmental chamber 205 may comprise a window 215 which allows monitoring the length of the crack in the at least one sample. The window 215 may comprise a double pane window or a wiper to prevent moisture condensation at sub-ambient temperatures.

In embodiments, the apparatus 200 may comprise a viewing device 220, such as a microscope or a video camera, to monitor the pre-applied crack length, a, and the onset of crack growth. Software, such as a pattern recognition routine, may be used to identify and describe the crack growth. The temperature of the environmental chamber and the length of the crack are recorded in an automated data acquisition and computing device, such as personal computer 225. The temperature at which the pre-applied crack, a, is observed to propagate through the width W of the at least one sample 5 causing sample fracture is the critical fracture temperature.

In embodiments, an electrically conductive line 230 may be placed on the at least one sample 5. Electrodes may be attached to the conductive line in a way known to those skilled in the art. The electrically conductive line 230 is of a size so as not to strengthen the at least one sample in any substantial way. The electrically conductive line 230 comprises an electrically conductive composite or a metal. The temperature of the environmental chamber 205 and the current through the conducting line 230 is monitored and recorded. When the at least one sample 5 fractures at the critical fracture temperature, the electrical circuit is interrupted. This method using the electrically conductive line eliminates the need for a viewing device 220 and window 215.

FIG. 4 is a schematic diagram of a sample 5 having the neck of the dog-bone according to an embodiment of the present invention. According to the present invention, the pre-applied crack, a, forces the failure of the sample to occur in the area where the crack was first made. To increase the thermally induced local stress and allow measurement of tough materials at convenient temperatures, it is advantageous to shorten the gage section 400 of the dog-bone shaped sample. To allow measurement of rather brittle samples, it is convenient to lengthen the neck or gage length 400 of the sample.

According to the present invention, the sample dimensions such as length, L, width, W, and initial crack length, a, may be used along with the measured critical fracture temperature to rank materials as follows.

In embodiments, the critical fracture temperature may be measured for several samples and plotted against the ratio of initial crack length over sample width, a/W. Differences in the initial crack length vary the value of the critical fracture temperature. It is advantageous to obtain data at several different a/W ratios. A critical fracture temperature for a particular a/W ratio may be obtained from a critical fracture temperature versus a/W curve, as show in FIG. 5. This value, the normalized critical fracture temperature, may be used to compare and rank the thermally induced fracture temperature of various material choices for a given application. The normalized thermally induced critical facture temperature is an indirect measure of the thermally induced fracture toughness of a material and can be considered to be a combinatorial reliability parameter combining the material's coefficient of thermal expansion (CTE), modulus, and thermal fracture toughness. Ranking materials by this criterion is of great practical value to increase the reliability of mechanical parts and structures which contain a material or combination of materials.

In embodiments, the thermal fatigue fracture of a material may be measured. The at least one sample and fixture assembly is subjected to a thermal cycle (heating and cooling between two set temperatures repeatedly). The number of cycles at which the at least one sample with particular a/W ratio breaks is a measure of the fatigue crack growth resistance or strength of the material. The number of cycles at which each sample with characterized a/W ratio breaks is recorded and plotted against the a/W ratio.

EXAMPLE

A sample comprising a highly filled epoxy polymer and having a pre-applied crack and a fixture comprising stainless steel and Invar were heated to 150° C. The sample was bonded to the fixture. The sample and fixture were cooled at 1° C./min and 4° C./min, respectively. Nitrogen gas convection was used during cooling to prevent any moisture effect. The crack growth of the sample was monitored and the temperature at which the onset of crack growth occurred (critical fracture temperature) was recorded. No mechanical stress was applied to the sample.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer-usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The exemplary and alternative embodiments described above may be combined in a variety of ways with each other. Furthermore, the steps and number of the various steps illustrated in the figures may be adjusted from that shown.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

What is claimed is:

1. A method for measuring the fracture and fatigue crack growth behavior of a material, comprising:

heating at least one sample having a first end and a second end and a pre-applied crack between the first end and the second end;

heating a fixture having a lower coefficient of thermal expansion than said at least one sample;

attaching the first end and the second end of the at least one sample to the fixture;

cooling the at least one sample and fixture;

recording the temperature at which propagation of the pre-applied crack through the width of the at least one sample occurs as the critical fracture temperature;

for a plurality of samples, each sample having a different ratio of pre-applied crack length to sample width, determining the critical fracture temperature as a function of said ratio; and ranking materials by the critical fracture temperature.

* * * * *